United States Patent [19]
Weng et al.

[11] Patent Number: 5,555,886
[45] Date of Patent: Sep. 17, 1996

[54] APPARATUS AND METHOD FOR DETECTING BLOOD VESSEL SIZE AND DIRECTION FOR DOPPLER FLOW MEASUREMENT SYSTEM

[75] Inventors: Lee Weng; William H. Phillips, both of Issaquah, Wash.

[73] Assignee: Siemens Medical Systems, Inc., Iselin, N.J.

[21] Appl. No.: 535,496

[22] Filed: Sep. 28, 1995

[51] Int. Cl.⁶ .................................................. A61B 8/00
[52] U.S. Cl. .................................................. 128/661.10
[58] Field of Search ................... 128/661.08, 661.09, 128/661.10, 660.04; 364/413.07, 413.25; 73/861.25, 861.26, 861.27

[56] References Cited

U.S. PATENT DOCUMENTS

| | | | |
|---|---|---|---|
| 4,370,985 | 2/1983 | Takeichi et al. | 128/661.10 |
| 4,800,891 | 1/1989 | Kim . | |
| 4,809,703 | 3/1989 | Ishikawa et al. . | |
| 4,961,427 | 10/1990 | Namekawa et al. . | |
| 5,150,292 | 9/1992 | Hoffmann et al. | 364/413.07 |
| 5,188,112 | 2/1993 | Sturgill et al. . | |
| 5,280,787 | 1/1994 | Wilson et al. | 128/661.1 |

OTHER PUBLICATIONS

L. S. Wilson et al., "Automatic Vessel Tracking And Measurment For Doppler Studies," *Ultrasound in Med. & Biol.*, vol. 16, No. 7, pp. 645–652, 1990.

*Primary Examiner*—George Manuel

[57] ABSTRACT

An ultrasonic diagnostic system is provided that automatically measures a volumetric flow rate of a vessel presented on a graphical display by estimating the vessel size and direction. The Doppler information signals received from an ultrasonic transducer include frequency components representing fluid flow through a region of interest. The operator selects a vessel represented graphically on the display in which a volumetric flow rate measurement is desired. The ultrasonic diagnostic system then performs a search in a plurality of directions that extend radially outward from a location within the vessel for an upper and a lower set of edge points that correspond to inner wall surfaces of the vessel. Once the upper and lower set of edge points are identified, curves are fitted through the respective sets of edge points to define respective estimates of the inner wall surfaces. Next, an angular difference between the respective curves and a beam direction of the Doppler information signals is measured. Finally, a volumetric flow rate measurement of the selected vessel can be derived within a region defined by the respective curves and based on the measured angular difference.

21 Claims, 2 Drawing Sheets

APPARATUS AND METHOD FOR DETECTING BLOOD VESSEL SIZE AND DIRECTION FOR DOPPLER FLOW MEASUREMENT SYSTEM

BACKGROUND OF THE INVENTION

1. Field of the Invention

The present invention relates to ultrasonic diagnostic imaging using Doppler shift measurement for detection and display of fluid flow velocities, and more particularly, to an imaging system that automatically calculates blood vessel size and flow velocity by use of a fuzzy logic technique.

2. Description of Related Art

Ultrasonic imaging techniques are commonly used to produce two-dimensional diagnostic images of internal features of an object, such as a human anatomy. A diagnostic ultrasonic imaging system for medical use forms images of internal tissues of a human body by electrically exciting an acoustic transducer element or an array of acoustic transducer elements to generate short ultrasonic pulses that travel into the body. The ultrasonic pulses produce echoes as they reflect off of body tissues that appear as discontinuities or impedance changes to the propagating ultrasonic pulses. These echoes return to the transducer, and are converted back into electrical signals that are amplified and decoded to produce a cross-sectional image of the tissues. These ultrasonic imaging systems are of significant importance to the medical field by providing physicians with real-time, high resolution images of the internal features of a human anatomy without resort to more invasive exploratory techniques, such as surgery.

The acoustic transducer which radiates the ultrasonic pulses typically comprises a piezoelectric element or matrix of piezoelectric elements. As known in the art, a piezoelectric element deforms upon application of an electrical signal to produce the ultrasonic pulses. In a similar manner, the received echoes cause the piezoelectric element to deform and generate the corresponding electrical signal. The acoustic transducer may be packaged within a handheld device that allows the physician substantial freedom to manipulate the transducer easily over a desired area of interest. The transducer would then be electrically connected via a cable to a central control device that generates and processes the electrical signals. In turn, the control device transmits the image information to a real-time viewing device, such as a video display terminal (VDT). The image information may also be stored to enable other physicians to view the diagnostic images at a later date.

One particular application of ultrasonic diagnostic imaging takes advantage of Doppler shift measurement to detect and display fluid flow velocities. In such a system, a region of interest within a patient is repetitively pulsed with ultrasonic signals, and the received echo signals are compared to a reference in order to determine a rate of flow of fluids through the region. The rate of flow can be determined from a measurement of the Doppler frequency shift of the received echo signals. As known in the art, the flow velocity can then be displayed within a colorized cross-sectional image in which different shading and color intensity represents flow rate and direction. These ultrasonic Doppler flow imaging systems are particularly useful in measuring volumetric blood flow through a vessel. In performing this type of circulatory system diagnosis, it is important to estimate the total volume of blood flow through the vessel rather than just the flow rate. If a portion of the artery were blocked due to stenosis or other such abnormal vascular condition, the blockage would appear as a substantial decrease in the blood flow volume.

Conventional Doppler flow imaging systems permit an operator to perform a volumetric blood flow estimation, albeit with a substantial level of manual intervention. The detected Doppler frequency shift is proportional to the blood velocity projection in the ultrasonic beam direction. In order to convert the measured speed to a volumetric flow measurement, it is necessary to first determine the angular difference between the direction of the ultrasonic beam and the direction of the vessel. Once the angular difference is known, the cross-sectional area of the vessel is estimated, and the volumetric flow rate determined by multiplying the estimated area with the mean velocity of the blood flow.

The angular difference is generally estimated by the ultrasound operator through visual interpretation of the image display. In a conventional ultrasound Doppler imaging system, the operator can manipulate a directional cursor on the image display to the center of a selected vessel in which a volumetric flow measurement is desired. The directional cursor is then rotated by the operator until its direction appears to coincide with the instantaneous linear direction of the vessel. Thereafter, the system calculates the angular difference based on the operator selected orientation of the directional cursor. Similarly, the cross-sectional area measurement of the vessel is based on an estimation of the vessel diameter by visually identifying the inner walls of the vessel on the image display. The operator then moves a pair of measurement cursors so that they appear to coincide with the inner vessel walls. The system then uses the distance between the measurement cursors to estimate the vessel inside diameter and cross-sectional area. From the estimated angular difference, estimated cross-sectional area, and mean velocity, the volumetric flow rate can be calculated.

Unfortunately, these visual estimation techniques are both unreliable and time consuming. The accuracy of the volumetric flow measurement is heavily dependent on the skill level of the operator. Even with a highly skilled operator, the directional and measurement cursors must be repositioned every time the transducer is moved to a new location. Any errors in the diameter estimation become magnified since the diameter is squared during the cross-sectional area calculation. To further complicate the diameter measurement, the vessel diameter may vary throughout a cardiac cycle. Finally, the existence of acoustic reverberations or other imaging artifacts that degrade image resolution tend to further increase the difficulty in visually identifying the orientation and position of the inner vessel walls.

Accordingly, a critical need exists for an ultrasonic diagnostic imaging system for detection and display of fluid flow velocities that is capable of accurately and automatically measuring the volumetric flow rate of a selected vessel. The imaging system should permit an operator to readily manipulate the transducer across a region of interest while obtaining an accurate volumetric flow measurement without having to continually reposition cursors on the display.

SUMMARY OF THE INVENTION

In accordance with the teachings of this invention, an ultrasonic diagnostic system is provided that automatically measures a volumetric flow rate of a selected vessel presented on a graphical display by estimating the vessel size and direction.

As in a conventional ultrasonic Doppler flow diagnostic system, the information signals received from an ultrasonic transducer include Doppler frequency components representing fluid flow through a region of interest. Unlike the conventional systems, however, the operator can obtain a volumetric flow rate measurement by simply selecting a vessel represented graphically on the display in which the volumetric flow rate measurement is desired. The ultrasonic diagnostic system then performs a search in a plurality of directions that extend radially outward from a location within the vessel to identify an upper and a lower set of edge points that correspond to inner wall surfaces of the vessel. Once the upper and lower set of edge points are identified, curves are fitted through the respective sets of edge points to define respective estimates of the inner wall surfaces. Next, an angular difference between the respective curves and a beam direction of the Doppler information signals is measured. Finally, a volumetric flow rate measurement of the selected vessel can be derived within a region defined by the respective curves and based on the measured angular difference.

To conduct the search in a plurality of directions, inner and outer search windows are defined that respectively encompass a plurality of pixels of the graphical display. The inner and outer search windows are moved in incremental steps outward along each of the radial directions, and a relative brightness value of the pixels encompassed within the respective inner and outer search windows is measured for each respective incremental movement. By evaluating the relative brightness values of the inner and outer search windows using a fuzzy logic technique, an estimated location of a particular edge point can be identified. According to the fuzzy logic technique, the edge point is reached when the outer search window has a relatively high brightness value and the inner search window has a relatively low brightness value. Alternatively, a relative color intensity value can be used instead of the relative brightness value in situations in which the vessel walls do not provide a sufficiently strong echo return signal to distinguish the wall on the basis of brightness.

DETAILED DESCRIPTION OF THE PREFERRED EMBODIMENT

Figures 1, 2, 3, 4:
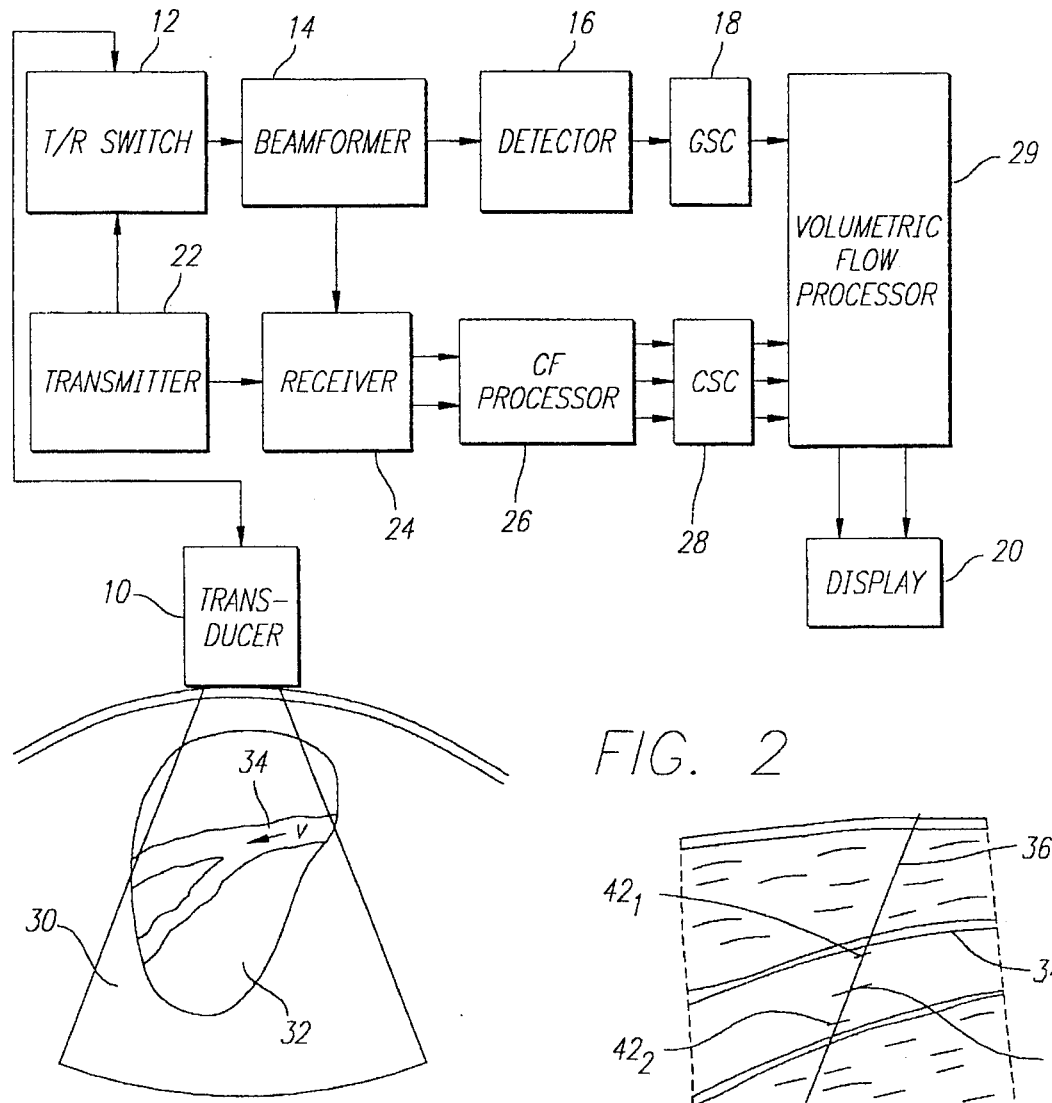
FIG. 1 is a block diagram of an ultrasonic diagnostic imaging apparatus of this invention.
FIG. 2 illustrates an exemplary Doppler flow image generated by a conventional ultrasonic diagnostic imaging apparatus.
FIG. 3 illustrates graphically a search for an upper and a lower set of edge points corresponding to inner wall surfaces of a vessel.
FIG. 4 illustrates graphically an estimate of the vessel diameter based on curves fitted through the upper and lower sets of edge points.

This invention satisfies the critical need for an ultrasonic diagnostic imaging system for detection and display of fluid flow velocities that is capable of accurately and automatically measuring the volumetric flow rate of a vessel. The imaging system permits an operator to readily manipulate the transducer across a region of interest while obtaining an accurate volumetric flow measurement without having to continually reposition cursors on the display. In the detailed description that follows, like reference numerals are used to describe like elements in one or more of the figures.

Referring first to FIG. 1, a block diagram of an ultrasonic diagnostic imaging apparatus of this invention is illustrated. A transmitter 22 generates a plurality of high frequency electronic signals that are amplified and provided to a piezoelectric transducer 10 through a transmit/receive (T/R) switch 12. The transducer 10 is comprised of a plurality of individual piezoelectric elements that are disposed in an array configuration. The transducer elements convert the respective electronic signals into ultrasonic pulsed waves that are coupled into an imaging region of interest 30 of a patient. The pulsed waves return to the transducer elements in the form of echo signals that are converted by the transducer elements back into high frequency electronic signals that are provided to a beamformer 14 through the T/R switch 12. The T/R switch 12 provides electrical isolation of the beamformer 14 during a transmit phase of the imaging apparatus.

In the illustration of FIG. 1, the region of interest 30 includes an exemplary organ 32 and a blood vessel 34. The echoes of the ultrasonic pulsed waves are received by the transducer 10, including relatively large amplitude echoes from the stationary tissue within the region of interest 30, and relatively small amplitude echoes from blood that is flowing with velocity V in the blood vessel 34. The beamformer 14 amplifies and digitizes the individual echo signals from each transducer element, adds an appropriate delay to the respective signals to account for relative path length differences, then combines the signals to produce a beamline signal which is applied as an input to a gray scale detector 16 and receiver 24. The gray scale detector 16 extracts a low frequency envelope signal from the beamline signal and transmits the low frequency envelope signal to a gray scale converter (GSC) 18. The gray scale converter 18 rearranges the scan order of the low frequency envelope signal and applies it to a display sub-system 20 that display a gray scale image in a manner that is well known in the art.

Since the echo signals from tissue within the region of interest are much stronger than the echo signals from blood flow in the vessel 34, the gray scale image of the blood flow is substantially obscured by the images of tissue features. In order to generate a color flow image of the blood flow, additional signal processing is necessary within the receiver 24 and a color flow (CF) processor 26. The receiver 24 down-converts the relatively high frequency RF beamline signals received from the beamformer 14 to relatively low frequency in-phase (I) and quadrature (Q) baseband signal samples using a reference RF signal from the transmitter 22, and transmits these I and Q signal samples to the color flow processor 26. The fluid flow velocity information contained in the I, Q signal samples is encoded as phase shifts in relation to the reference RF signal. The color flow processor 26 develops estimates of various parameters of the I, Q signal samples representative of movement in the scanned area and provides these estimates to a color flow scan converter (CSC) 28. The color flow scan converter 28 converts the scanning order of the estimated parameters to a format suitable for forming a color flow image and provides the parameters to the display sub-system 20.

Referring now to FIG. 2, an exemplary Doppler flow image generated by a conventional ultrasonic diagnostic imaging apparatus is provided. The Doppler flow image represents a two-dimensional planar slice of a region of interest below a skin layer of a patient as it would be graphically displayed on a display sub-system 20. A Doppler beam direction line 36 is illustrated graphically on the image display, and represents the steered direction of the plurality of ultrasonic pulsed waves emitted by the transducer 10. The Doppler flow image includes a portion of a vessel 34 in which an operator desires to make a volumetric blood flow rate measurement.

In the conventional ultrasonic imaging apparatus of FIG. 2, a flow direction cursor 38 is provided that can be manipulated by the operator into a desired location. In particular, the flow direction cursor 38 can be moved along the Doppler beam directional line 36 into a position in which the desired flow measurement will be made. The operator selects a desired vessel by moving the flow direction cursor 38 until it appears to be approximately centered within the vessel 34. Once the desired vessel is selected, the flow direction cursor 38 can be rotated about an axis defined by the intersection of the direction cursor with the Doppler beam directional line 36. The operator rotates the flow direction cursor 38 until its direction appears to coincide with the instantaneous direction of the vessel 34. The adjusted position of the flow direction cursor 38 defines an angle θ that is used to calculate the flow velocity v of fluid within the vessel 34, which can be calculated by the following equation:

$$v = \frac{f_d c}{2 f_0 \cos\theta}$$

in which $f_d$ represents the Doppler frequency shift, $f_0$ is the transmitted ultrasound frequency, c is the speed of sound, and θ is the Doppler beam angle. It can be presumed that the blood flows parallel with the blood vessel, so that the angle θ is approximately equal to the angle between the blood vessel walls and the Doppler beam directional line 36.

Next, a pair of measurement cursors $42_1$, $42_2$ are used to define a diameter measurement of the vessel 34. Like the flow direction cursor 38, the measurement cursors $42_1$, $42_2$ intersect with the Doppler beam directional line 36, and are disposed equidistant from the flow direction cursor. The operator can vary the relative positions of the measurement cursors $42_1$, $42_2$ until they appear to coincide with the inner wall surfaces of the vessel 34. The selected positions of the measurement cursors $42_1$, $42_2$ are utilized to calculate a diameter value of the vessel 34 that is used in conjunction with the angle θ determined above to calculate the volumetric flow rate measurement.

Specifically, the distance between the measurement cursors $42_1$, $42_2$ defines a gate width G that relates to the vessel diameter D by the following equation:

$$G = \frac{D}{\sin\theta}$$

The volumetric flow rate VF relates to the product of the cross-sectional area of the vessel and the mean flow velocity $\bar{v}$ of fluid within the vessel by the following equation:

$$VF = \frac{\pi D^2 \bar{v}}{4}$$

As known in the art, the respective positions and orientations of the flow direction cursor 38 and the measurement cursors $42_1$, $42_2$ are manipulated by the operator using manual control devices, such as computer keys or a track ball. As a result, the accuracy of the volumetric flow measurement is dependent almost entirely on the ability of the operator to accurately position these cursors with respect to the image of the selected vessel. As the transducer 10 is relocated or the beam re-steered by the operator during routine imaging operations, the Doppler beam directional line 36 shifts and the displayed image changes accordingly. The operator must then manually relocate the flow direction cursor 38 and the measurement cursors $42_1$, $42_2$ for the changed image conditions. As noted above, this procedure is cumbersome, time consuming, and prone to significant error in the ultimate volumetric flow rate measurement. This invention solves each of these problems.

In this invention, a volumetric flow processor 29 (see FIG. 1) receives inputs from the gray scale converter 18 and the color flow scan converter 28 to automatically estimate the volumetric flow rate. Referring next to FIGS. 3 and 4, a method for calculating the angle θ and diameter D is provided that completely avoids these disadvantages of the conventional visual estimation techniques. As in the previous method, the operator selects a vessel for volumetric flow rate measurement by moving a cursor into the desired vessel. As will be clear by the description that follows, however, it is not necessary that the cursor be precisely positioned at the center of the vessel; the operator need only position the cursor within the vessel. Moreover, the operator need not estimate the angle of the vessel or the position of the vessel inner walls, since these estimations will be performed automatically by the ultrasonic diagnostic imaging apparatus, as will be described below.

Specifically, FIG. 3 illustrates a process for estimating the angle of the vessel 34 with respect to the Doppler beam directional line 36. From an initial position of the cursor 38, a plurality of radial lines $E_1$–$E_5$ are extended outwardly until they respectively intersect with the inner vessel walls. For example, radial line $E_1$ intersects with an upper vessel wall surface at edge point $P_1$, and with a lower vessel wall surface at edge point $P_{10}$. In a similar manner, radial line $E_2$ intersects with the respective vessel walls at edge points $P_2$ and $P_9$; radial line $E_3$ intersects with the respective vessel walls at edge points $P_3$ and $P_8$; radial line $E_4$ intersects with the respective vessel walls at edge points $P_4$ and $P_7$; and, radial line $E_5$ intersects with the respective vessel walls at edge points $P_5$ and $P_6$. The edge points $P_1$–$P_5$ define an upper set of edge points, and the edge points $P_6$–$P_{10}$ define a lower set of edge points.

The upper and lower sets of edge points are used to estimate the inner wall surfaces of the vessel 34. For ease of calculation, it can be assumed that over a short length the vessel 34 lies in a straight line and the upper and lower edges of the vessel are parallel. While an actual blood vessel has unique and unpredictable curvature and shape, the curves are usually moderate and seldom very abrupt. Accordingly, a straight line assumption is considered reasonably accurate. By use of a conventional curve fitting algorithm, such as a least squares (L-S) method, line segments $44_1$ and $44_2$ are defined that pass through the upper and lower sets of edge points, respectively. Once the line segments $44_1$, $44_2$ are defined, the angle θ with respect to the Doppler beam directional line 36 is measured. Each of the line segments $44_1$, $44_2$ are compared to the Doppler beam directional line 36 to measure angles $\theta_1$, $\theta_2$, respectively, and the final angle θ represents the average of $\theta_1$ and $\theta_2$. It should be apparent that averaging the angles $\theta_1$, $\theta_2$ tends to mitigate any inaccuracy of the initial line segment placement.

FIG. 4 illustrates a process for estimating the diameter D of the vessel 34. A plurality of line segments $D_1$–$D_5$ are extended between corresponding ones of the edge points $P_1$–$P_{10}$. Particularly, line segment $D_1$ extends between edge points $P_1$ and $P_6$; line segment $D_2$ extends between edge points $P_2$ and $P_7$; line segment $D_3$ extends between edge points $P_3$ and $P_8$; line segment $D_4$ extends between edge points $P_4$ and $P_9$; and line segment $D_5$ extends between edge points $P_5$ and $P_{10}$. The length of each one of the line segments $D_1$–$D_5$ is measured and averaged, yielding the diameter measurement D. More specifically, the vessel diameter can be expressed by the following equation:

$$D = \frac{1}{n} \sum_{i=1}^{n} D_i$$

where n represents the total number of line segments $D_n$. As with the angle measurement described above, averaging the diameter measurements tends to mitigate any inaccuracy of the initial line segment placement.

Note also that five radial lines $E_1$–$E_5$, ten edge points $P_1$–$P_{10}$ and five line segments $D_1$–$D_5$ are shown for illustrative purposes only, and it should be apparent that a lesser or greater number could also be advantageously used. While a greater number would increase the accuracy of the estimations, the associated amount of computation would also increase. Accordingly, it may be desirable to enable an operator to selectively control this aspect of the estimation process so that the level of accuracy can be appropriately matched with the particular diagnosis.

In the preceding description, the edge points $P_1$–$P_{10}$ are defined at the intersections between the inner vessel walls and the radial lines $E_1$–$E_5$. As with the visual estimation techniques described above, it is very difficult in practice to accurately discern these intersections, especially where image resolution is poor or other such imaging artifacts are present. Moreover, it is difficult to implement such a method within an electronic system since the image variations can be rather complex.

Accordingly, the search for the vessel wall intersections can be efficiently quantized by use of a fuzzy logic system. There are certain known characteristics of the vessel wall intersections that can aid in the search. In particular, it is known that the ultrasound echo signals returned from the vessel walls are far stronger than the signals returned from the blood moving within the vessels. As a result, the displayed image of the blood appears very dark or black, while the vessel wall is more bright with large vessels producing a particularly bright image. In addition, the surrounding tissue outside the vessel also produces a relatively bright image. Thus, the fuzzy logic system can locate the edge points by identifying a boundary between the dark and bright image regions.

Figure 5:
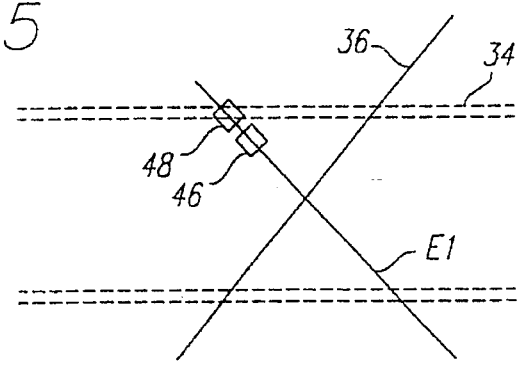
FIG. 5 illustrates inner and outer search windows used to estimate edge point locations by a fuzzy logic technique.

In FIG. 5, the vessel 34 is illustrated as in FIGS. 3 and 4 with the Doppler beam directional line 36 extending therethrough. Note that the broken lines of the vessel 34 illustrates a graphically ambiguous vessel inner wall boundary requiring identification. The first radial line $E_1$ extends outwardly from an operator selected point within the vessel 34. Two search windows are defined, including an inner search window 46 and an outer search window 48, and are moved in slight increments along the radial line to search for the edge points. Each of the search windows 46, 48 encompass a small region that includes a plurality of pixels of the graphical display. An average brightness value is derived from the pixels within each of the search windows 46, 48, and the respective average brightness values are compared for each incremental position of the search windows along the radial line. The edge point is effectively located when the inner and outer search windows 46, 48 straddle opposite sides of the demarcation between dark and bright image regions. The search process is then repeated for the other direction of the radial line $E_1$ to identify the lower vessel wall surface, as well as for each one of the other radial lines $E_2$–$E_5$ of FIG. 3.

Specifically, a fuzzy logic control unit within the volumetric flow processor 29 receives brightness values I(i), O(i) for the respective inner and outer search windows as inputs, combines them using fuzzy rules (described below), and produces a single numerical output C(i) which represents a confidence value of the likelihood of an edge point. The brightness values I(i), O(i) range from zero, which represents minimum brightness, to one, which represents maximum brightness. Also, the numerical output C(i) ranges from zero to one, with the confidence that an edge point is reached increasing as the numerical output approaches one. The inputs I(i) and O(i) are first "fuzzified" into the linguistic expressions, or labels, "high", "medium" and "low". Output C(i) also has its fuzzy expressions of "high", "medium", and "low".

Figure 6A:
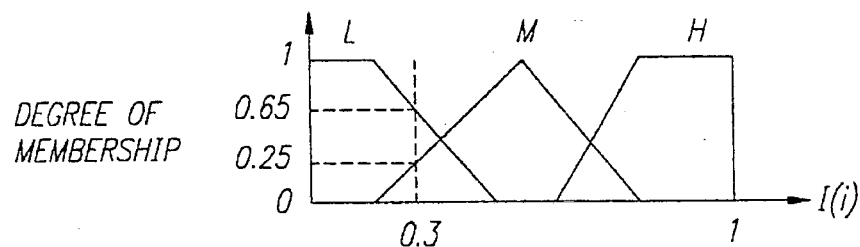
FIGS. 6a–c are graphs illustrating fuzzy logic membership functions of inner and outer search windows for identifying the vessel edge points.
Figure 6B:
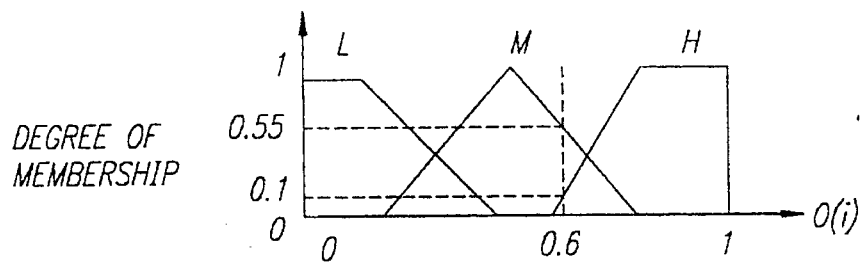
Figure 6C:
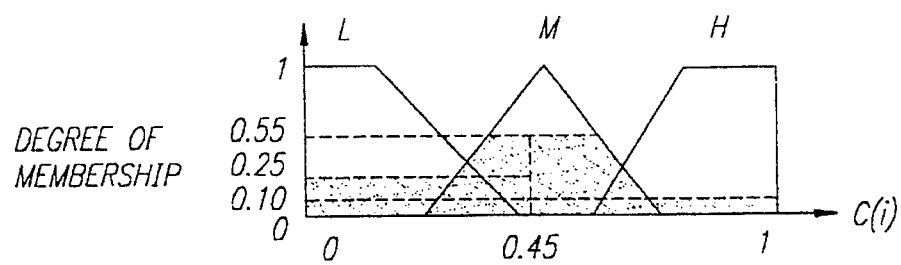

Membership functions of I(i), O(i) and C(i) are defined from a large number of experimental results, and are illustrated at FIGS. 6a through 6c, respectively. The membership function of I(i) is graphically illustrated at FIG. 6a as comprising three regions labeled as L (low), M (medium) and H (high). The regions overlap to a certain extent; specifically, the L and M regions overlap, and the M and H regions overlap. The horizontal axis of the membership function graph defines the measured value of I(i), and the vertical axis defines the degree of membership of the measured value within the defined label. The membership function of O(i) is graphically illustrated at FIG. 6b, and is constructed similar to the membership function of I(i). Similarly, the membership function of C(i) is graphically illustrated at FIG. 6c, and is constructed similar to the membership functions of I(i) and O(i).

Six fuzzy rules are used to define the relationship between I(i), O(i) and C(i). These fuzzy rules include:

(1) If I(i) is high (H), then C(i) is low (L);

(2) If O(i) is low (L), then C(i) is low (L);

(3) If I(i) is medium (M) AND O(i) is medium (M), then C(i) is low (L);

(4) If I(i) is low (L) AND O(i) is medium (M), the C(i) is medium (M);

(5) If I(i) is medium (M) AND O(i) is high (H), then C(i) is medium (M);

(6) If I(i) is low (L) AND O(i) is high (H), then C(i) is high (H).

The fuzzy rules are applied in parallel to determine the truth of the rules. For example, assume that measured values of I(i) and O(i) are 0.3 and 0.6, respectively. In FIG. 6a, a measured value of 0.3 relates to degrees of membership of approximately 0.65 in the L label and approximately 0.25 in the M label. In FIG. 6b, a measured value of 0.6 relates to a degree of membership of approximately 0.1 in the H label and approximately 0.55 in the M label. As a result, only the last four fuzzy rules are true, though they yield inconsistent results. Particularly, the third fuzzy rule concludes C(i) is low, the fourth and fifth fuzzy rules conclude C(i) is medium, and the sixth fuzzy rule concludes that C(i) is high. The output C(i) must be converted back to a numerical value, and the inconsistent results must be reconciled.

Under the third fuzzy rule, the medium value of I(i) is combined using a logical AND with the medium value of O(i) to provide the low value of C(i). Under the logical AND operation, the minimum value of the truth of the expressions is taken as the truth level of the rule. In other words, the 0.25 degree of membership of I(i) is less than the 0.55 degree of membership of O(i), and is thus taken as the truth level for the first fuzzy rule. Similarly, under the fourth fuzzy rule, the low value of I(i) is combined using a logical AND with the medium value of O(i) to provide the medium value of C(i). The 0.55 degree of membership of O(i) is less than the 0.65 degree of membership of I(i), and is thus taken as the truth level for the fourth fuzzy rule. Under the fifth fuzzy rule, the medium value of I(i) is combined using a logical AND with the high value of O(i) to provide the medium value of C(i). The 0.10 degree of membership of O(i) is less than the 0.25 degree of membership of I(i), and is taken as the truth level for the fifth fuzzy rule. Finally, under the sixth fuzzy rule, the low value of I(i) is combined using a logical AND with the high value of O(i) to provide the high value of C(i). The 0.10 degree of membership of O(i) is less than the 0.65 degree of membership of I(i), and is taken as the truth level for the fifth fuzzy rule. The L, M and H labels of the C(i) membership function are then truncated at the truth levels defined by the fuzzy rules, as illustrated graphically in FIG. 6c.

A centroid defuzzification technique is used to convert the fuzzy output back to a numerical number C(i). Using this technique, an estimate of the center of gravity is provided for the entire region determined to be true (illustrated as the shaded region of FIG. 6c). The center of gravity of the shaded region is approximately 0.45, providing a numerical confidence value for C(i). In a similar manner, confidence values for a plurality of incremental positions of the inner and outer search windows 46, 48 for both directions of each radial line $E_1$–$E_5$. A local maximum confidence value is most likely to coincide with the respective edge point $P_1$–$P_{10}$.

Once each of the edge points $P_1$–$P_{10}$ are located, the vessel angle θ is estimated using the process described previously with respect to FIG. 3. The diameter D is then estimated using the process described previously with respect to FIG. 4. Finally, the mean velocity $\bar{v}$ and volumetric flow rate VF are calculated using the equations set forth above.

Under certain circumstances, the brightness values of I(i) and O(i) from the inner and outer search windows may yield inconclusive results and may not be usable to identify the edge points. This situation may occur where the acoustic return signal from the vessel and/or surrounding tissue is very weak, and the vessel wall cannot be distinguished by consideration of brightness. Since the color flow process is generally more sensitive to the relatively weak Doppler return signal, it is possible to utilize the color generated by the color flow processor as a vessel wall indicator, instead of brightness. In such an embodiment, the color flow image will approximate the blood vessel boundary.

In an alternative embodiment of this invention, the color intensity measurement is used instead of the brightness value in the fuzzy logic process described above. The color intensity value would be inversely proportional to the brightness value, because the edge points are located at the region where color intensity drops off. For this process to function properly, it may also be necessary to utilize color flow image data that is collected in a so-called "persistence mode" of operation, so that a near constant color intensity output is derived. As known in the art, periodic variations in blood flow velocity that are common in pulsed arterial blood flow will cause the color intensity values to oscillate. In the persistence mode of operation, an average color intensity is displayed rather than the periodic color flashing. The average color intensity values could then be advantageously utilized in the fuzzy logic process to identify the edge points.

The invention is defined by the following claims.

What is claimed is:

1. In an ultrasonic diagnostic system, including means for receiving Doppler information signals having frequency components representing fluid flow through a region of interest, and means for formatting said Doppler information signals for presentation on a graphical display, a method for measuring a volumetric flow rate of a vessel within the region of interest comprising the steps of:

selecting a vessel represented graphically on the display in which a volumetric flow rate measurement is desired;

searching in a plurality of directions that extend radially outward from a location defined within the selected vessel for an upper and a lower set of edge points that correspond to inner wall surfaces of the vessel;

fitting curves through the respective sets of edge points that define respective estimates of the inner wall surfaces;

measuring an angular difference between the respective curves and a beam direction of the Doppler information signals; and deriving a volumetric flow rate measurement of the selected vessel within a region defined by the respective curves and based on the measured angular difference.

2. The method of claim 1, wherein the step of selecting a vessel further comprises the step of manipulating a cursor on the display until the cursor is approximately centered in the selected vessel.

3. The method of claim 1, wherein the step of searching in a plurality of directions further comprises the steps of:

defining inner and outer search windows that respectively encompass a plurality of pixels of said display;

moving the inner and outer search windows outward in increments along each of the directions;

deriving a relative measurement value of the pixels within the respective inner and outer search windows;

comparing the relative measurement values of the inner and outer search windows using a fuzzy logic technique; and repeating the moving, measuring and comparing steps until a particular edge point is located.

4. The method of claim 3, wherein the step of comparing the relative measurement values further comprises the step of defining membership functions for the inner and outer search windows.

5. The method of claim 4, wherein the step of comparing the relative measurement values further comprises the step of determining a membership value for the inner and outer search windows.

6. The method of claim 5, wherein the step of comparing the relative measurement values further comprises the step of combining the membership values for the inner and outer search windows in accordance with predefined fuzzy rules to generate an output value.

7. The method of claim 3, wherein the step of deriving a relative measurement value further comprises the step of deriving a relative brightness value.

8. The method of claim 3, wherein the step of deriving a relative measurement value further comprises the step of deriving a relative color intensity value.

9. The method of claim 1, wherein said step of deriving a volumetric flow rate measurement further comprises the step of measuring a diameter of the selected vessel.

10. The method of claim 9, wherein said step of measuring a diameter further comprises the step of measuring an average distance between associated ones of the edge points of the upper and lower sets.

11. The method of claim 9, wherein said step of deriving a volumetric flow rate measurement further comprises the step of estimating a cross-sectional area of the selected vessel based on the measured diameter.

12. The method of claim 11, wherein said step of deriving a volumetric flow rate measurement further comprises the step of multiplying the estimated cross-sectional area with the cosine of the measured angular difference.

13. An ultrasonic diagnostic system, including means for receiving Doppler information signals having frequency components representing fluid flow through a region of interest, and means for formatting said Doppler information signals for presentation on a graphical display, comprising:

means for selecting a vessel represented graphically on the display in which a volumetric flow rate measurement is desired;

means for searching in a plurality of directions that extend radially outward from a location defined within the selected vessel for an upper and a lower set of edge points that correspond to inner wall surfaces of the vessel;

means for fitting curves through the respective sets of edge points that define respective estimates of the inner wall surfaces;

means for measuring an angular difference between the respective curves and a beam direction of the Doppler information signals; and means for deriving a volumetric flow rate measurement of the selected vessel within a region defined by the respective curves and based on the measured angular difference.

14. The system of claim 13, wherein the searching means further comprises:

means for defining inner and outer search windows that respectively encompass a plurality of pixels of said display;

means for moving the inner and outer search windows outward in increments along each of the directions;

means for measuring a relative value of the pixels within the respective inner and outer search windows; and means for comparing the relative measurement values of the inner and outer search windows using a fuzzy logic technique.

15. The system of claim 14, wherein the comparing means further comprises means for determining a membership value for the inner and outer search windows.

16. The system of claim 15, wherein the comparing means further comprises means for combining the membership values for the inner and outer search windows in accordance with predefined fuzzy rules to generate an output value.

17. The system of claim 13, wherein said deriving means further comprises means for measuring a diameter of the selected vessel.

18. The system of claim 17, wherein said means for measuring a diameter further comprises means for measuring an average distance between associated ones of the edge points of the upper and lower sets.

19. The system of claim 17, wherein said deriving means further comprises means for estimating a cross-sectional area of the selected vessel based on the measured diameter.

20. The system of claim 14, wherein said relative value further comprises a relative brightness value.

21. The method of claim 14, wherein said relative value further comprises a relative color intensity value.

* * * * *